(12) United States Patent
Beard et al.

(10) Patent No.: US 7,737,173 B2
(45) Date of Patent: Jun. 15, 2010

(54) INDOLE-3-CARBOXYLIC ACID AMIDE, ESTER, THIOAMIDE AND THIOL ESTER COMPOUNDS BEARING ARYL OR HETEROARYL GROUPS HAVING SPHINGOSINE-1-PHOSPHATE (S1P) RECEPTOR ANTAGONIST BIOLOGICAL ACTIVITY

(75) Inventors: Richard L. Beard, Newport Beach, CA (US); John E. Donello, Dana Point, CA (US); Haiqing Yuan, Irvine, CA (US); Diana F. Colon, Newport Beach, CA (US); Tien Duong, Rancho Santa Margarita, CA (US); Xiaoxia Liu, Lake Forest, CA (US); Yihui Hu, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 24 days.

(21) Appl. No.: 11/675,168

(22) Filed: Feb. 15, 2007

(65) Prior Publication Data
US 2007/0191313 A1 Aug. 16, 2007

Related U.S. Application Data

(60) Provisional application No. 60/774,102, filed on Feb. 15, 2006.

(51) Int. Cl.
A61K 31/40 (2006.01)
C07D 209/42 (2006.01)
(52) U.S. Cl. ...................... 514/419; 548/492
(58) Field of Classification Search ...................... None
See application file for complete search history.

(56) References Cited

U.S. PATENT DOCUMENTS

| | | | |
|---|---|---|---|
| 4,952,683 | A | 8/1990 | Tschannen et al. |
| 5,102,901 | A | 4/1992 | van Wijngaarden et al. |
| 5,110,987 | A | 5/1992 | Liotta et al. |
| 5,294,722 | A | 3/1994 | Kim |
| 5,403,851 | A | 4/1995 | D'Orlando et al. |
| 5,580,878 | A | 12/1996 | D'Orlando et al. |
| 5,994,378 | A | 11/1999 | Matsuo et al. |
| 6,235,912 | B1 | 5/2001 | Takesako et al. |
| 6,239,297 | B1 | 5/2001 | Takesako et al. |
| 2003/0125371 | A1 | 7/2003 | Elokdah et al. |
| 2003/0220319 | A1 | 11/2003 | Greenhouse et al. |

FOREIGN PATENT DOCUMENTS

| | | |
|---|---|---|
| DE | 19753522 | 6/1999 |
| FR | 2121394 | 8/1972 |
| JP | 2007-126454 | 5/2007 |
| WO | WO00/42045 | 7/2000 |
| WO | WO01/98301 | 12/2001 |
| WO | WO03/070691 | 8/2003 |
| WO | WO2006/066879 | 6/2006 |

OTHER PUBLICATIONS

Nakamura et al., Bioorg & Med Chem 15 (2007), 3548-3564.*
Yasuhiro Gon, et al., "S1P3 receptor-induced reorganization of epithelial tight junctions compromises lung barrier integrity and is potentiated by TNF," PNAS, Jun. 28, 2005, vol. 102, No. 26, pp. 9270-9275.
Kellie A. Park, et al., "Lipid mediators of sensitivity in sensory neurons," Review, TRENDS in Pharmacological Sciences, vol. 26, No. 11 Nov. 2005, pp. 571-577.
Carlock, John T., et al., 3-Diazo-4-Oxo-3,4-Dihydroquinoline, A Novel Synthon for Indole-3-Carboxamides, J.Org.Chem, vol. 42, No. 11, 1977 (XP002444824).
Clayden, Jonathan, et al., "Nucleophilic Additon to Electron-Rich Heteroaromatics: Dearomatizing Anionic Cyclizations of Pyrrolecarboxamides," Organic Letters vol. 6, N. 4, 2004, pp. 609-611 (XP002444823).
Bajwa, Joginder S., "Chemoselective Deprotection of Benzyl Esters in the Presence of Benzyl Ethers, Benzyloxymethyl Ethers and N-Benzyl Groups by Catalytic Transfer Hydrogenation," Tetrahedron Letters, vol. 33, No. 17, 1992, pp. 2299-2302 (XP002444822).
Chemical Abstracts Service (XP002444828).
DiSanto, Roberto, et al., "N-(1-Naphthylmethyl)-N-(1-Alkyl-4-Aryl-1H-Pyrrol-3-YL Methyl)Methylamines Related to Naftifine. Systehsis and Antifungal Activity," Med. Chem Res 7:2 (1997) 98-108 (XP002958012).
Kutschy, Peter, et al., "Synthesis of Some Analogs of Indole Phytoalexins Brassinin and Methoxybrassenin B and Their Positional Isomers," Collect. Czech. Chem. Commun. vol. 64, 1999 (XP002276545).

(Continued)

Primary Examiner—Golam M. M. Shameem
Assistant Examiner—Sun Jae Y Loewe
(74) Attorney, Agent, or Firm—Kevin J. Forrestal; John E. Wurst; Allergan, Inc.

(57) ABSTRACT

The invention provides compounds represented by the formula I, each of which compounds may have sphingosine-1-phosphate receptor agonist and or antagonist biological activity:

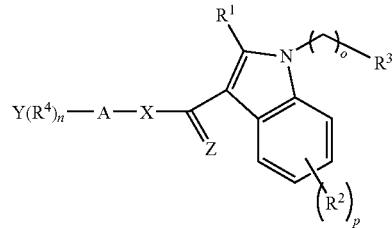

and wherein the variables Y, $R^4$, n, A, X, Z, $R^1$, o, $R^3$, $R^2$ and p are as defined in the specification. These compounds are useful for treating a disease or condition selected from the group consisting of glaucoma, dry eye, angiogenesis, cardiovascular conditions and diseases, and wound healing.

3 Claims, No Drawings

OTHER PUBLICATIONS

Domschke, Gunter, et al., "N-Substituierte 1-Benz1-2-Methyl-3-Aminomethyl-5-Methoxy-Indole," Chemische Berichte, Verlag Chemie GMBH. Weinheim, De, vol. 93, pp. 2097-2106, 1960 (XP000961036).

Chemical Abstracts (XP002444827).

Sauer, Daryl R., et al., "Microwave-Assisted Synthesis Utilizing Supported Reagents: A Rapid and Efficient Acylation Procedure," Organic Letters, vol. 5, No. 24, 2003, pp. 4721-4724 (XP002444821).

Nagashima, Tadamichi, et al., "Fluorous 2-Chloropyridinium Salt (Mukaiyama Condensatioon Reagent) for Amide Formation Reactions," Tetrahedron Letters, Elsevier, Amsterdam, NL, vol. 46, No. 38, 2005, pp. 6585-6588 (XP005034771).

* cited by examiner

INDOLE-3-CARBOXYLIC ACID AMIDE, ESTER, THIOAMIDE AND THIOL ESTER COMPOUNDS BEARING ARYL OR HETEROARYL GROUPS HAVING SPHINGOSINE-1-PHOSPHATE (S1P) RECEPTOR ANTAGONIST BIOLOGICAL ACTIVITY

CROSS REFERENCE TO RELATED APPLICATIONS

This application is based on, and claims the benefit of, U.S. Provisional Application No. 60/774,102, filed Feb. 15, 2006, and which is incorporated herein by reference.

BACKGROUND OF THE INVENTION

1. Field of the Invention

The present invention relates to derivatives and/or analogues of sphingosine and pharmaceutical compositions, including such derivatives and/or analogues, which are useful as drugs for the treatment of fungal infections, allergic diseases, immune disorders, etc.

2. Summary of the Art

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

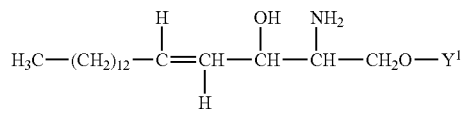

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by spingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 µM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or spingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

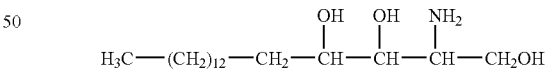

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

Derivatives of sphingosine have been prepared in various patents. For example, see U.S. Pat. Nos. 4,952,683; 5,110,987; 6,235,912 B1 and 6,239,297 B1.

Also, compounds which are similar to certain spingosine derivatives, but which are not reported as being ligands for the spingosine receptors are reported in various patents and published patent applications. See for example, U.S. Pat. Nos. 5,294,722; 5,102,901; 5,403,851 and 5,580,878. U.S. Patent Application Publication No. U.S. 2003/0125371 A2. While certain of the compounds reported in the above patents are indoles, it does not appear that indole compounds have been reported as being ligands for sphingosine receptor or having activity as sphingosine agonists or antagonists.

SUMMARY OF THE INVENTION

The present invention provides a derivative or analogue of sphingosine that is able to regulate the functions of sphingolipid, and pharmaceutical compositions comprising said derivative or analogue.

These compounds are represented by the formula I, each of which compounds may have sphingosine-1-phosphate receptor agonist and or antagonist biological activity:

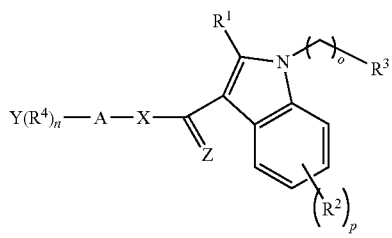

wherein:
X is $NR^5$, O, S;
Z is O or S;
n is 0 or an integer of from 1 to 4;
o is 0 or an integer of from 1 to 3;
p is 0 or an integer of from 1 to 4;
A is $(C(R^5)_2)m$, wherein
m is 0 or an integer of from 1 to 6;
$R^5$ is selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl (as defined below), halo, $C_1$ to $C_{12}$ haloalkyl, hydroxyl, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, or sulfonyl groups;
Y is a carbocyclic aryl or heterocyclic aryl group wherein said carbocylic aryl comprises from 6 to 20 atoms and said heterocyclic aryl comprises from 2 to 20 carbon atoms and from 1 to 5 heteroatoms selected from the group consisting of nitrogen, oxygen and sulfur, and wherein said aryl may be bonded to A at any position;
$R^1$, $R^2$, $R^3$, $R^4$ are selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl (as defined below), halo, $C_1$ to $C_{12}$ haloalkyl, hydroxyl, $C_1$ to $C_{12}$ alkoxy, $C_3$ to $C_{20}$ arylalkyloxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, or sulfonyl groups, or a group selected from the group consisting of:

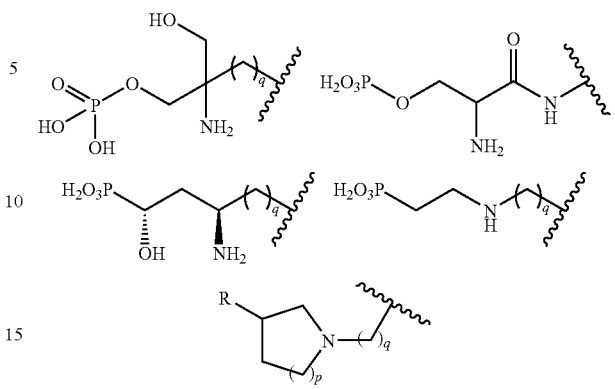

wherein R is $CO_2H$ or $PO_3H_2$, p is an integer of 1 or 2 and q is 0 or an integer of 1 to 5.

The aryl group is a carbocyclic aryl or heterocyclic aryl group wherein said carbocylic aryl comprises from 6 to 20 atoms and said heterocyclic aryl comprise from 2 to 20 carbon atoms and from 1 to 5 heteroatoms selected from the group consisting of nitrogen, oxygen and sulfur, and preferably said aryl group is selected from the group consisting of benzene, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalen, chromene, thiochromene, dihydroquinoline, indan, dihydrobenzofuran, dihydrobenzothiophene, indene, benzofuran, benzothiophene, coumarin and coumarinone. Said aryl groups can be bonded to the above moiety at any position. Said aryl group may itself be substituted with any common organic functional group including but not limited to $C_1$ to $C_{12}$ alkyl, $C_2$ to $C_6$ alkenyl, $C_2$ to $C_6$ alkynyl, halo, $C_1$ to $C_{12}$ haloalkyl, hydroxyl, $C_1$ to $C_{12}$ alkoxyl, $C_1$ to $C_{12}$ alkylcarbonyl, formyl, oxycarbonyl, carboxyl, $C_1$ to $C_{12}$ alkyl carboxylate, $C_1$ to $C_{12}$ alkyl amide, aminocarbonyl, amino, cyano, diazo, nitro, thio, sulfoxyl, or sulfonyl groups.

Preferably Z is O.

Preferably, the carbocyclic aryl group will comprise from 6 to 14 carbon atoms, e.g. from 6 to 10 carbon atoms. Preferably the heterocyclic aryl group will comprise from 2 to 14 carbon atoms and one or more, e.g. from 1 to 3 heteroatoms selected from the group consisting of nitrogen, oxygen and sulfur.

Specific Examples of the compounds of formula I include

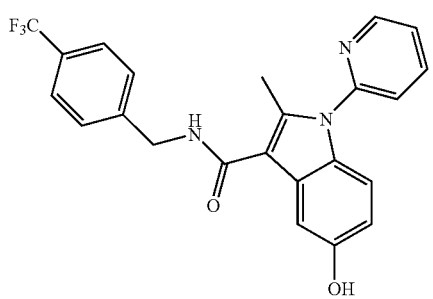

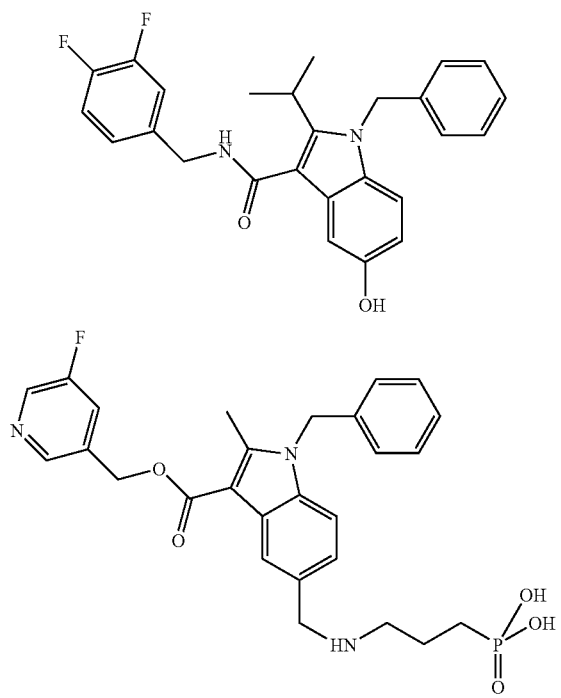

These compounds may be synthesized as illustrated by the synthesis scheme below:

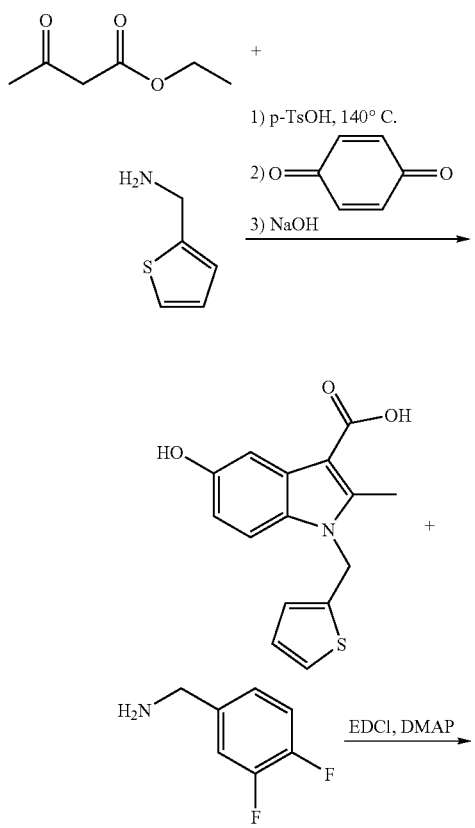

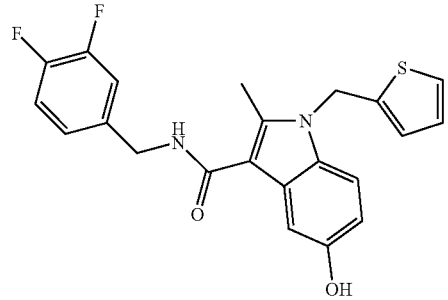

In general, a beta-ketoester (e.g. ethyl acetoacetate) is treated with an amine (e.g. 2-thiophenemethyl amine) in the presence of an organic acid (e.g. para-toluenesulfonic acid) and 1,4-benzoquinone to produce a 5-hydroxyindole-3-carboxylic acid (e.g. 5-hydroxy-2-methyl-1-(2-thiophenemethyl)indole-3-carboxylic acid) after hydrolysis of the ester with a strong base such as sodium hydroxide in a suitable solvent such as ethanol. The carboxylic acid is further reacted with an amine in the presence of N-(3-dimethylaminopropyl)-N'-ethylcarbodimide (EDC) to produce 5-hydroxyindole-3-carboxamide (e.g. 3,4-difluorophenylmethyl 5-hydroxy-2-methyl-1-(2-thiophenemethyl)indole-3-carboxamide). The carboxylic acid may also be treated with an alcohol or thiol in the presence of EDC to produce an ester and thiol ester derivatives, respectively,

DETAILED DESCRIPTION OF THE INVENTION

Unless otherwise indicated, the following terms as used throughout this specification have the following meanings:

"Me" refers to methyl.
"Et" refers to ethyl.
"tBu" refers to t-butyl.
"iPr" refers to i-propyl.
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino and SH.

"Alkenyl" refers to a straight-chain, branched or cyclic unsaturated hydrocarbon group containing at least one carbon—carbon double bond. Preferably, the alkenyl group has 2 to 12 carbons. More preferably it is a lower alkenyl of from 2 to 7 carbons, most preferably 2 to 4 carbons. The alkenyl group may be optionally substituted with one or more substituents selected from the group consisting of hydroxyl, cyano, alkoxy, O, S, $NO_2$, halogen, dimethyl amino and SH.

"Alkynyl" refers to a straight-chain, branched or cyclic unsaturated hydrocarbon containing at least one carbon—carbon triple bond. Preferably, the alkynyl group has 2 to 12 carbons. More preferably it is a lower alkynyl of from 2 to 7 carbons, most preferably 2 to 4 carbons. The alkynyl group may be optionally substituted with one or more substituents selected from the group consisting of hydroxyl, cyano, alkoxy, O, S, $NO_2$, halogen, dimethyl amino and SH.

"Alkoxy" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Aryloxy" refers to an "O-aryl" group.

"Arylalkyloxy" refers to an "O-alkaryl" group.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Ester" refers to —C(O)—O—R', wherein R' is alkyl, aryl or alkylaryl.

"Thioamide" refers to —C(S)—NH—R', wherein R' is alkyl, aryl, alkylaryl or hydrogen.

"Thiol ester" refers to —C(O)—S—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$ —R"", where R"" is aryl, C(CN)=C-aryl, $CH_2$ CN, alkyaryl, sulfonamide, NH-alkyl, NH-alkylaryl, or NH-aryl.

Also, alternatively the substituent on the phenyl moiety, as shown below, is referred to as an o, m or p substituent or a 2, 3 or 4 substituent, respectively. (Obviously, the 5 substituent is also a m substituent and the 6 substituent is an o substituent.)

Specific compounds of the invention and their selectivity are at the sphingosine-1-phosphate receptors reported in Table I, below.

Compounds were assessed for their ability to activate or block activation of the human S1P3 receptor in T24 cells stably expressing the human S1P3 receptor. Ten thousand cells/well were plated into 384-well poly-D-lysine coated plates one day prior to use. The growth media for the S1P3 receptor expressing cell line was McCoy's 5A medium supplemented with 10% charcoal-treated fetal bovine serum (FBS), 1% antibiotic-antimycotic and 400 µg/ml geneticin. On the day of the experiment, the cells were washed twice with Hank's Balanced Salt Solution supplemented with 20 mM HEPES (HBSS/Hepes buffer). The cells were then dye loaded with 2 uM Fluo-4 diluted in the HBSS/Hepes buffer with 1.25 mM Probenecid and incubated at 37° C. for 40 minutes. Extracellular dye was removed by washing the cell plates four times prior to placing the plates in the FLIPR (Fluorometric Imaging Plate Reader, Molecular Devices). Ligands were diluted in HBSS/Hepes buffer and prepared in 384-well microplates. The positive control, Sphingosine-1-Phosphate (SIP), was diluted in HBSS/Hepes buffer with 4 mg/ml fatty acid free bovine serum albumin. The FLIPR transferred 12.5 µl from the ligand microplate to the cell plate and took fluorescent measurements for 75 seconds, taking readings every second, and then for 2.5 minutes, taking readings every 10 seconds. Drugs were tested over the concentration range of 0.61 nM to 10,000 nM. Data for $Ca^{+2}$ responses were obtained in arbitrary fluorescence units and not translated into $Ca^{+2}$ concentrations. $IC_{50}$ values were determined through a linear regression analysis using the Levenburg Marquardt algorithm.

TABLE I

| Compound Number | S1P Receptor Antagonist Activity | |
|---|---|---|
| | Structure | S1P3 $IC_{50}$ (% eff.) |
| 1 | [structure] | NA |
| 3 | [structure] | 0.51 µM (53) |
| 4 | [structure] | 1.7 µM (66) |

TABLE I-continued

S1P Receptor Antagonist Activity

| Compound Number | Structure | S1P3 IC$_{50}$ (% eff.) |
|---|---|---|
| 5 | 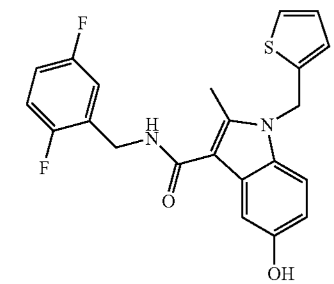 | ND |
| 6 | 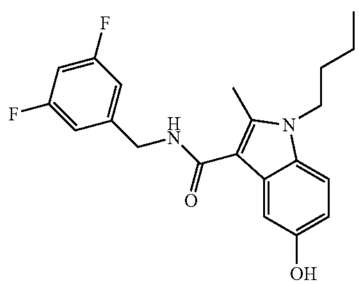 | 2.5 μM (55) |
| 7 | 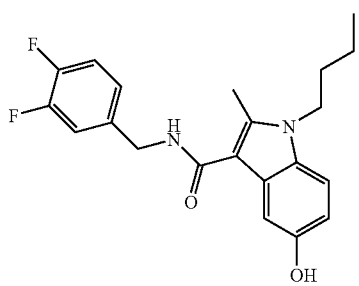 | ND |
| 8 | 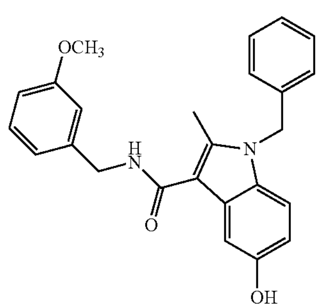 | ND |
| 9 | 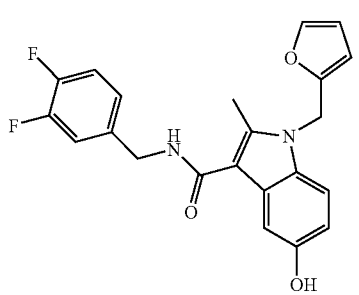 | 2.9 μM (97) |
| 10 | 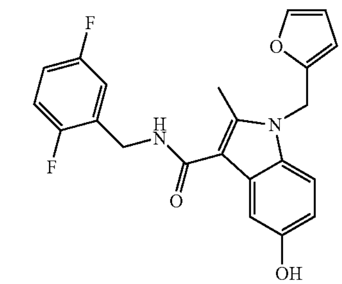 | ND |
| 11 | 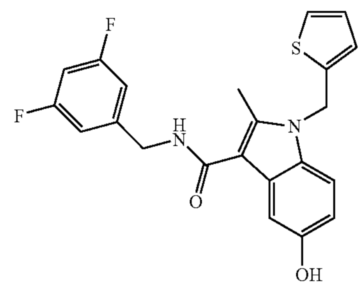 | 1.8 μM (67) |
| 12 | 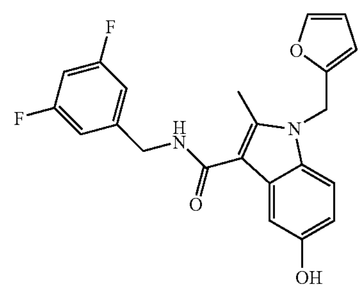 | 0.95 μM (77) |
| 13 | 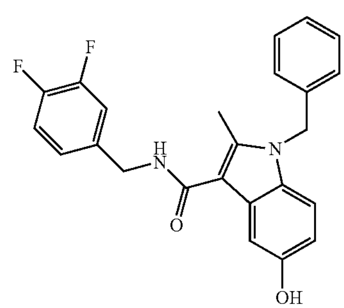 | 1.5 μM (84) |
| 14 | 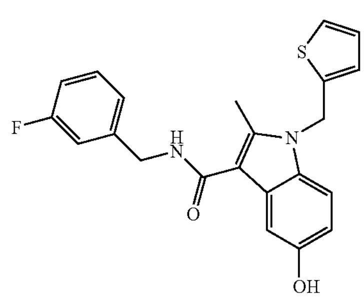 | 3.2 μM (85) |

TABLE I-continued

S1P Receptor Antagonist Activity

| Compound Number | Structure | S1P3 IC$_{50}$ (% eff.) |
|---|---|---|
| 15 | (N-benzyl-2-methyl-1-(thiophen-2-ylmethyl)-5-hydroxy-1H-indole-3-carboxamide) | 1.6 μM (48) |
| 16 | (N-(2-fluorobenzyl)-2-methyl-1-(thiophen-2-ylmethyl)-5-hydroxy-1H-indole-3-carboxamide) | NA |
| 17 | (N-(3-methoxybenzyl)-2-methyl-1-(thiophen-2-ylmethyl)-5-hydroxy-1H-indole-3-carboxamide) | 0.91 μM (33) |
| 18 | (N-(3-methoxybenzyl)-1-butyl-2-methyl-5-hydroxy-1H-indole-3-carboxamide) | 5.1 μM (42) |
| 19 | (N-(4-fluorobenzyl)-2-methyl-1-(thiophen-2-ylmethyl)-5-hydroxy-1H-indole-3-carboxamide) | 2.7 μM (72) |
| 20 | (N-(4-methylbenzyl)-2-methyl-1-(thiophen-2-ylmethyl)-5-hydroxy-1H-indole-3-carboxamide) | 2.5 μM (71) |
| 21 | (N-(3-chlorobenzyl)-2-methyl-1-(thiophen-2-ylmethyl)-5-hydroxy-1H-indole-3-carboxamide) | 1.2 μM (38) |
| 22 | (N-(4-chlorobenzyl)-2-methyl-1-(thiophen-2-ylmethyl)-5-hydroxy-1H-indole-3-carboxamide) | 2.5 μM (83) |
| 23 | (N-(2-methoxybenzyl)-2-methyl-1-(thiophen-2-ylmethyl)-5-hydroxy-1H-indole-3-carboxamide) | 2.4 μM (23) |
| 24 | (N-(3-trifluoromethylbenzyl)-2-methyl-1-(thiophen-2-ylmethyl)-5-hydroxy-1H-indole-3-carboxamide) | NA |
| 25 | (N-(3,4-difluorobenzyl)-2-ethyl-1-benzyl-5-hydroxy-1H-indole-3-carboxamide) | 0.7 μM (98) |

TABLE I-continued

S1P Receptor Antagonist Activity

| Compound Number | Structure | S1P3 IC$_{50}$ (% eff.) |
|---|---|---|
| 26 | 3-methoxybenzyl amide, 2-ethyl, 1-benzyl, 5-OH indole-3-carboxamide | 1.9 μM (97) |
| 27 | 3,4-difluorobenzyl amide, 1-benzyl, 5-OH indole-3-carboxamide | NA |
| 28 | 3,4-difluorobenzyl amide, 2-isopropyl, 1-benzyl, 5-OH indole-3-carboxamide | 55 nM (98) |
| 29 | 3,4-difluorobenzyl amide, 2-methyl, 1-phenyl, 5-OH indole-3-carboxamide | 9.7 μM (76) |
| 30 | 3,4-difluorobenzyl amide, 2-methyl, 1-(2-pyridyl), 5-OH indole-3-carboxamide | 1.5 μM (23) |
| 31 | 3,4-difluorobenzyl amide, 2-methyl, 1-(2-thienyl), 5-OH indole-3-carboxamide | 2.5 μM (81) |
| 32 | 3,5-difluorobenzyl amide, 2-ethyl, 1-benzyl, 5-OH indole-3-carboxamide | 0.28 μM (97) |
| 33 | 3,5-difluorobenzyl amide, 2-isopropyl, 1-benzyl, 5-OH indole-3-carboxamide | 0.11 μM (99) |
| 34 | 3-methoxybenzyl amide, 2-isopropyl, 1-benzyl, 5-OH indole-3-carboxamide | 0.41 μM (98) |
| 35 | 3,5-difluorobenzyl amide, 2-methyl, 1-phenyl, 5-OMe indole-3-carboxamide | NA |
| 36 | 3,5-difluorobenzyl amide, 2-methyl, 1-benzyl indole-3-carboxamide | NA |
| 37 | 3,4-difluorobenzyl amide, 2-methyl, 1-benzyl indole-3-carboxamide | NA |

TABLE I-continued

S1P Receptor Antagonist Activity

| Compound Number | Structure | S1P3 IC$_{50}$ (% eff.) |
|---|---|---|
| 38 | 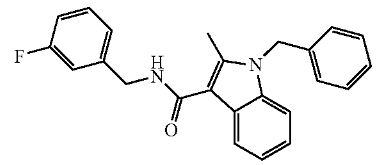 | NA |
| 39 | 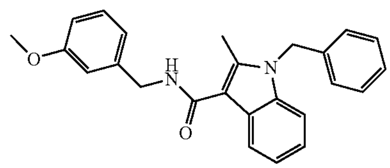 | NA |
| 40 | 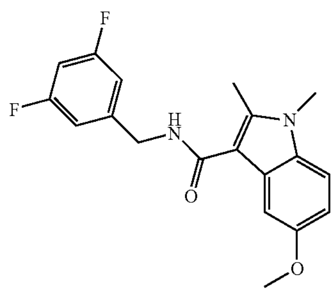 | NA |
| 41 | 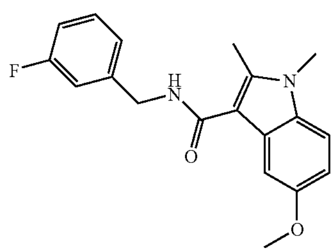 | NA |
| 42 | 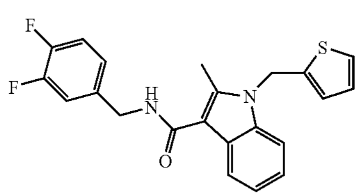 | NA |
| 43 | 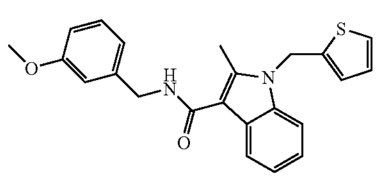 | NA |
| 44 | 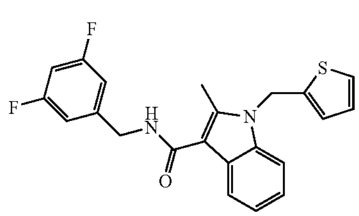 | NA |
| 45 | 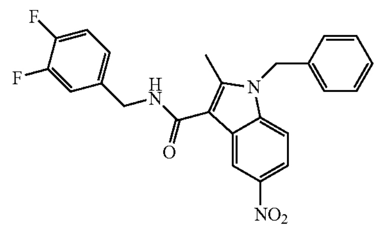 | NA |
| 46 | 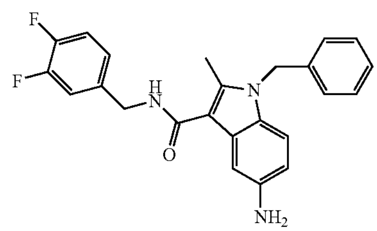 | NA |
| 47 | 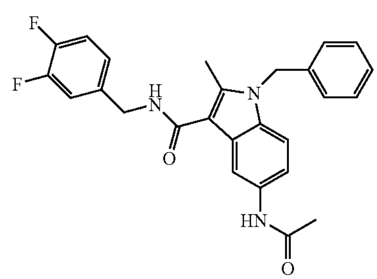 | NA |
| 48 | 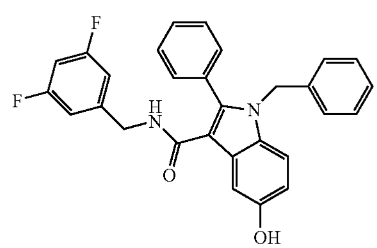 | 0.88 μM (98) |
| 49 | 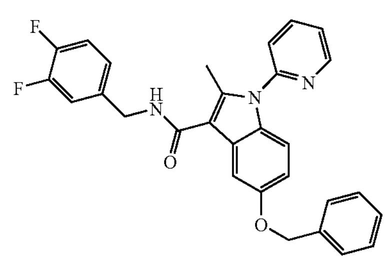 | NA |

As a result of the above activity of the compounds utilized in the method of the present invention, it is clear that such compounds may be used in treating the following diseases and conditions for the following reasons.

Glaucoma

S1P3 subtypes are expressed in primary human trabecular meshwork cells and S1P decreases outflow facility >30% in perfused porcine eyes (See IOVS 45, 2263; 2004) by altering paracellular permeability.

Dry Eye/Immunology

Induces lymphocyte sequestration without affecting T cell proliferation.

Angiogenesis Disorders

S1P3 receptor subtype is expressed in vascular endothelial cells and siRNA knockdown of S1P1 and S1P3 inhibits angiogenesis. S1P also promotes vascular endothelial cell migration and promotes barrier assembly and integrity.

Cardiovascular (S1P3)

S1P3 "knock out" mice lack S1P induced pulmonary edema.

The invention is further illustrated by the following examples which are illustrative of a specific mode of practicing the invention and are not intended as limiting the scope of the claims.

Unless otherwise indicated, the following Chemical Abbreviations are used in the examples:

NaOH: sodium hydroxide
EtOH: ethanol
HCl: hydrogen chloride
EtOAc: ethyl acetate
$Na_2SO_4$: sodium sulfate
MeOH: methanol
Pd-C: palladium on activated carbon
$Et_2O$: diethyl ether
EDC: N-(3-Dimethylaminopropyl)-N'-ethylcarbodiimide hydrochloride
HOBT: 1-hydroxybenzotriazole
$CH_2Cl_2$: methylene chloride
DMF: N,N-dimethylformamide
DCC: N,N'-dicyclohexylcarbodiimide
DMSO: dimethylsulfoxide Benzylamine, benzyl bromide, n-butylamine,3-chlorobenzylamine,4-chlorobenzylamine, furfuryl amine,2,5-difluorobenzylamine,3,4-difluorobenzylamine, 3,5-difluorobenzylamine, iodobenzene,2-iodopyridine,2-iodothiophene, ethyl acetoacetate, ethyl benzoylacetate, ethyl5-hydroxy-2-methylindole-3-carboxylate, ethyl isobutyrylacetate, ethyl3-oxovelarate,2-fluorobenzylamine, 3-fluorobenzylamine,4-fluorobenzylamine,2-methoxybenzylamine, 3-methoxybenzylamine,4-methylbenzylamine,2-thiophenemethylamine and3-(trifluoromethyl)benzylamine were purchased from Aldrich Chemical Company.

5-Benzyloxyindole-3-carboxaldehyde was purchased from Sigma Chemical Company.

2-Methyl-5-nitro-1H-indole-3carboxaldehyde was purchased from Fisher Scientific Company.

Scheme 1

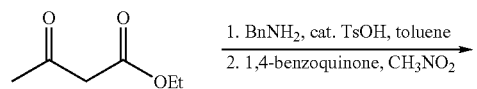

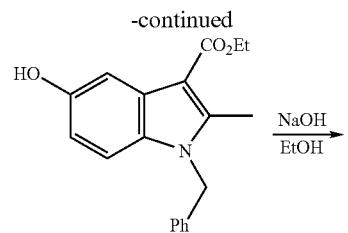

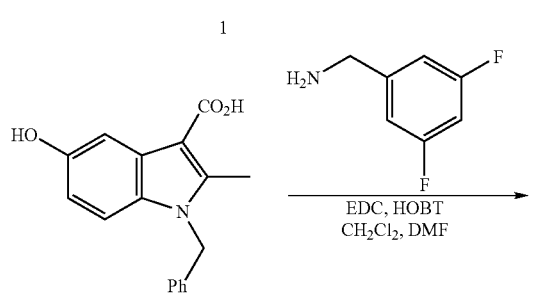

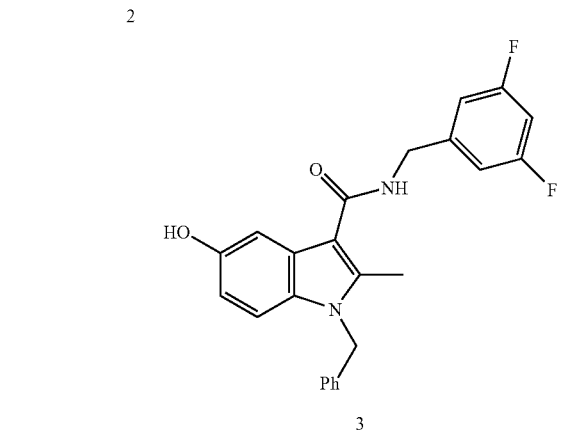

EXAMPLE 1

Ethyl 1-Benzyl-5-hydroxy-2-methyl-1H-indole-3-carboxylate (Compound 1)

General Procedure 1. To a solution of ethyl acetoacetate (1.3 ml, 10 mmol) and benzylamine (1.2 ml, 10.5 mmol) in toluene (10 ml) was added p-toluenesulfonic acid monohydrate (95 mg, 0.5 mmol). The mixture was heated at 140° C. to reflux for 4 h, cooled to 0° C. and filtered. The filtrate was concentrated under reduced pressure to give a yellow oil (2.6 g). To a solution of 1,4-benzoquinone (1.49 g, 13.8 mmol) in nitromethane (5 ml) was added a solution of the above yellow oil in nitromethane (3.5 ml) slowly. The resulting mixture was stirred at room temperature for 18 h and was cooled to 0° C. and filtered. The solid was washed with cold nitromethane to yield ethyl 1-benzyl-5-hydroxy-2-methyl-1H-indole-3-carboxylate (Compound 1) as a beige solid.

$^1$H-NMR (CHLOROFORM-d) δ 1.45(t, J=7.0 Hz, 3 H), 2.70 (s, 3 H), 4.40 (q, J=7.2 Hz, 2 H), 5.09 (s, 1 H), 5.31 (s, 2 H), 6.75 (dd, J=8.6, 2.5 Hz, 1 H), 6.92-7.01 (m, 2 H), 7.08 (d, J=8.8 Hz, 1 H), 7.23-7.32 (m, 3 H), 7.65 (d, J=2.6 Hz, 1 H).

EXAMPLE 2

1-Benzyl-5-hydroxy-2-methyl-1H-indole-3-carboxylic Acid (Compound 2)

General Procedure 2 A solution of ethyl 1-benzyl-5-hydroxy-2-methyl-1H-indole-3-carboxylate (Compound 1, 873 mg, 2.83 mmol) and NaOH (2.2 g, 56 mmol) in EtOH (10 ml) and $H_2O$ (10 ml) was heated to 90° C. for 16 h. The reaction was quenched with 6M HCl (10 ml), extracted with EtOAc, washed with brine, dried over $Na_2SO_4$, and concentrated under reduced pressure. The residue was purified by flash column chromatography on silica gel (30% EtOAc-hexanes to 20% MeOH-EtOAc) to yield 1-benzyl-5-hydroxy-2-methyl-1H-indole-3-carboxylic acid (Compound 2) as a reddish brown solid.

$^1$H-NMR (METHANOL-$d_4$) δ 2.67 (s, 3 H), 5.41 (s, 2 H), 6.68 (dd, J=8.8, 2.3 Hz, 1 H), 6.96-7.03 (m, 2 H), 7.15 (d, J=8.8 Hz, 1 H), 7.20-7.32 (m, 3 H), 7.55 (d, J=2.1 Hz 1 H).

EXAMPLE 3

1-Benzyl-5-hydroxy-2-methyl-1H-indole-3-carboxylic Acid, 3,5-Difluorobenzylamide (Compound 3)

General Procedure 3. To a solution of 1-benzyl-5-hydroxy-2-methyl-1H-indole-3-carboxylic acid (Compound 2, 205 mg, 0.73 mmol) in $CH_2Cl_2$ (5 ml) and DMF (3 ml) was added EDC (211 mg, 1.1 mmol), HOBT (149 mg, 1.1 mmol) and 3,5-difluorobenzylamine (260 μl, 2.2 mmol). The mixture was stirred at room temperature for 16 h, diluted with EtOAc, and washed with 1M HCl, and brine, and dried over $Na_2SO_4$, and concentrated under reduced pressure. The residue was purified by flash column chromatography on silica gel (30% to 50% EtOAc-hexanes) to yield 1-benzyl-5-hydroxy-2-methyl-1H-indole-3-carboxylic acid, 3,5-difluorobenzylamide (Compound 3) as a beige solid.

$^1$H-NMR (METHANOL-$d_4$) δ 2.57 (s, 3 H), 4.61 (s, 2 H), 5.40 (s, 2 H), 6.70 (dd, J=8.8, 2.3 Hz, 1 H), 6.77-6.88 (m, 1 H), 6.97-7.07 (m, 4 H), 7.14-7.19 (m, 1 H), 7.20-7.32 (m, 4 H).

The following compounds were prepared using General Procedures 1, 2 and 3 and the appropriate amines and beta-ketoester starting materials, which are available from Aldrich Chemical Company or prepared as described below:

EXAMPLE 4

5-Hydroxy-2-methyl-1-thiophen-2-ylmethyl-1H-indole-3-carboxylic Acid, 3,4-Difluorobenzylamide (Compound 4)

$^1$H-NMR (ACETONE-$d_6$) δ 2.73 (s, 3 H), 4.64 (d, J=6.1 Hz, 2 H), 5.59 (s, 2 H), 6.77 (dd, J=8.5, 2.0 Hz, 1 H), 6.93-7.01 (m, 2 H), 7.25-7.40 (m, 6 H), 7.88 (br s, 1 H).

EXAMPLE 5

5-Hydroxy-2-methyl-1-thiophen-2-ylmethyl-1H-indole-3-carboxylic Acid, 2,5-Difluorobenzylamide (Compound 5)

$^1$H-NMR (ACETONE-$d_6$) δ 2.74 (s, 3 H), 4.68 (d, J=5.9 Hz, 2 H), 5.59 (s, 2 H), 6.77 (dd, J=8.8, 2.4 Hz, 1 H), 6.93-7.33 (m, 6 H), 7.38 (d, J=15.6 Hz, 2 H), 7.9 (br s, 1 H).

EXAMPLE 6

1-Butyl-5-hydroxy-2-methyl-1H-indole-3-carboxylic Acid, 3,5-Difluoro-benzylamide (Compound 6)

$^1$H-NMR (CHLOROFORM-d) δ 0.95 (t, J=7.5 Hz, 3 H), 1.38 (m, 2 H), 1.70 (m, 2 H), 2.69 (s, 3 H), 4.03 (t, J=7.5 Hz, 2 H), 4.59 (d, J=6.1 Hz, 2 H), 5.81 (s, 1 H), 6.23 (br t, 1 H), 6.66 (m, 1 H), 6.80 (dd, J=2.2, 8.8 Hz, 1 H), 6.86 (br d, 2 H), 7.15 (br d, 2 H).

EXAMPLE 7

1-Butyl-5-hydroxy-2-methyl-1H-indole-3-carboxylic Acid, 3,4-Difluoro-benzylamide (Compound 7)

$^1$H-NMR (CHLOROFORM-d) δ 0.95 (t, J=7.5 Hz, 3 H), 1.36 (m, 2 H), 1.70 (m, 2 H), 2.69 (s, 3 H), 4.03 (t, J=7.5 Hz, 2 H), 4.58 (d, J=6.1 Hz, 2 H), 5.75 (s, 1 H), 6.20 (br t, 1 H), 6.76 (dd, J=2.6, 8.8 Hz, 1 H), 7.05-7.16 (m, 5 H).

EXAMPLE 8

1-Benzyl-5-hydroxy-2-methyl-1H-indole-3-carboxylic Acid, 3-Methoxybenzylamide (Compound 8)

$^1$H-NMR (CHLOROFORM-d) δ 2.67 (s, 3 H), 3.81 (s, 3 H), 4.67 (d, J=5.6 Hz, 2 H), 5.30 (s, 2 H), 6.17 (t, J=5.6 Hz, 1 H), 6.73 (dd, J=8.8, 2.3 Hz, 1 H), 6.83 (dd, J=7.8, 2.2 Hz, 1 H), 6.94-7.02 (m, 4 H), 7.09 (d, J=9.1 Hz, 1 H), 7.22 (d, J=2.3 Hz, 1 H), 7.23-7.33 (m, 4 H).

EXAMPLE 9

1-Furan-2-ylmethyl-5-hydroxy-2-methyl-1H-indole-3-carboxylic Acid, 3,4-Difluorobenzylamide (Compound 9)

$^1$H-NMR (ACETONE-$d_6$) δ 2.78 (s, 3 H), 4.64 (d, J=6.1 Hz, 2 H), 5.38 (s, 2 H), 6.34-6.37 (m, 2 H), 6.74 (dd, J=8.8, 2.3 Hz, 1 H), 7.23-7.45 (m, 6 H), 7.81 (s, 1 H).

EXAMPLE 10

1-Furan-2-ylmethyl-5-hydroxy-2-methyl-1H-indole-3-carboxylic Acid, 2,5-Difluorobenzylamide (Compound 10)

$^1$H-NMR (ACETONE-$d_6$) δ 2.77 (s, 3 H), 4.68 (d, J=6.1 Hz, 2 H), 5.38 (s, 2 H), 6.34-6.39 (m, 2 H), 6.77 (dd, J=8.8, 2.3 Hz, 1 H), 7.04-7.33 (m, 3 H), 7.39 (d, J=16.1 Hz, 2 H), 7.45 (d, J=2.6 Hz, 1 H), 7.88 (b s, 1 H).

EXAMPLE 11

5-Hydroxy-2-methyl-1-thiophen-2-ylmethyl-1H-indole-3-carboxylic Acid, 3,5-Difluorobenzylamide (Compound 11)

$^1$H-NMR (ACETONE-$d_6$) δ 2.78 (s, 3 H), 4.66 (d, J=6.2 Hz, 2 H), 5.59 (s, 2 H), 6.74 (dd, J=8.8, 2.4 Hz, 1 H), 6.80-7.02 (m, 3 H), 7.08 (d, J=8.8Hz, 1 H), 7.28 (d, J=2.4 Hz, 1 H), 7.32 (d, J=5.0 Hz, 1 H), 7.38 (d, J=16 Hz, 2 H), 7.42 (b s, 1 H).

EXAMPLE 12

1-Furan-2-ylmethyl-5-hydroxy-2-methyl-1H-indole-3-carboxylic Acid 3,5-Difluorobenzylamide (Compound 12)

$^1$H-NMR (ACETONE-$d_6$) δ 2.78 (s, 3 H), 4.66 (d, J=6.2 Hz, 2 H), 5.38 (s, 2 H), 6.34-6.39 (m, 2 H), 6.74 (dd, J=8.8, 2.4 Hz, 1 H), 6.80-6.90 (m, 1 H), 7.08 (dd, J=8.8, 2.4 Hz, 1 H), 7.23-7.32 (m, 3 H), 7.27 (d, J=2.4 Hz, 1 H) 7.42 (d, J=15.9 Hz, 2 H), 7.45 (d, J=2.1 Hz, 1 H), 7.84 (s, 1 H).

EXAMPLE 13

1-Benzyl-5-hydroxy-2-methyl-1H-indole-3-carboxylic Acid, 3,4-Difluoro-benzylamide (Compound 13)

$^1$H-NMR (METHANOL-$d_4$) δ 2.55 (s, 3 H), 4.57 (s, 2 H), 5.38 (s, 2 H), 6.69 (dd, J=2.2, 8.8 Hz, 1 H), 6.99 (2 br d, 2 H), 7.16 (d, J=8.8 Hz, 1 H), 7.17-7.30 (m, 7 H).

EXAMPLE 14

5-Hydroxy-2-methyl-1-thiophen-2-ylmethyl-1H-indole-3-carboxylic Acid, 3-Fluorobenzylamide (Compound 14)

$^1$H-NMR (METHANOL-$d_4$) δ 2.65 (s, 3 H), 4.60 (s, 2 H), 5.52 (s, 2 H), 6.73 (dd, J=2.2, 8.8 Hz, 1 H), 6.90-7.00 (m, 3 H), 7.10-7.39 (m, 6 H).

EXAMPLE 15

5-Hydroxy-2-methyl-1-thiophen-2-ylmethyl-1H-indole-3-carboxylic Acid, Benzylamide (Compound 15)

$^1$H-NMR (METHANOL-$d_4$) δ 2.64 (s, 3 H), 4.60 (s, 2 H), 5.52 (s, 2 H), 6.72 (dd, J=2.2, 8.8 Hz, 1 H), 6.91 (2 br d, 2 H), 7.16 (d, J=2.2 Hz, 1 H), 7.24-7.27 (m, 2 H), 7.31 (d, J=4.0 Hz, 1 H), 7.35 (d, J=7.0 Hz, 2 H), 7.42 (d, J=7.5 Hz, 2 H).

EXAMPLE 16

5-Hydroxy-2-methyl-1-thiophen-2-ylmethyl-1H-indole-3-carboxylic Acid, 2-Fluorobenzylamide (Compound 16)

$^1$H-NMR (METHANOL-$d_4$) δ 2.67 (s, 3 H), 4.69 (s, 2 H), 5.55 (s, 2 H), 6.72 (dd, J=2.6, 8.8 Hz, 1 H), 6.94 (m, 2 H), 7.40 (m, 1 H), 7.20 (m, 2 H), 7.28 (m, 1 H), 7.32 (overlap m, 1 H), 7.32 (d, J=8.8 Hz, 1 H), 7.50 (t, J=7.5 Hz, 1 H).

EXAMPLE 17

5-Hydroxy-2-methyl-1-thiophen-2-ylmethyl-1H-indole-3-carboxylic Acid, 3-Methoxybenzylamide (Compound 17)

$^1$H-NMR (METHANOL-$d_4$) δ 2.68 (s, 3 H), 3.81 (s, 3 H), 4.61 (s, 2 H), 5.55 (s, 2 H), 6.75 (dd, J=2.6, 8.8 Hz, 1 H), 6.85 (dd, J=2.5, 8.4 Hz, 1 H), 6.94 (m, 2 H), 7.02 (2 br d, 2 H), 7.19 (d, J=2.5 Hz, 1 H), 7.28 (m, 2 H), 7.32 (d, J=8.7 Hz, 1 H).

EXAMPLE 18

1-Butyl-5-hydroxy-2-methyl-1H-indole-3-carboxylic Acid, 3-Methoxy-benzylamide (Compound 18)

$^1$H-NMR (METHANOL-$d_4$) δ 0.95 (t, J=7.5 Hz, 3 H), 1.39 (m, 2 H), 1.71 (m, 2 H), 2.60 (s, 3 H), 3.78 (s, 3 H), 4.11 (t, J=7.5 Hz, 2 H), 4.58 (s, 2 H), 6.72 (dd, J=2.2, 8.8 Hz, 1 H), 7.03 (dd, J=2.2, 8.4 Hz, 1 H), 6.90 (2 br d, 2 H), 7.15 (d, J=2.2 Hz, 1 H), 7.21 (d, J=8.8 Hz, 1 H), 7.26 (d, J=8.4 Hz, 1 H).

EXAMPLE 19

5-Hydroxy-2-methyl-1-thiophen-2-ylmethyl-1H-indole-3-carboxylic Acid, 4-Fluorobenzylamide (Compound 19)

$^1$H-NMR (METHANOL-$d_4$) δ 2.63 (s, 3 H), 4.58 (s, 2 H), 5.53 (s, 2 H), 6.72 (dd, J=2.6, 8.8 Hz, 1 H), 6.91 (2 br d, 2 H), 7.06 (t, J=8.8 Hz, 2 H), 7.15 (d, J=2.2 Hz, 1 H), 7.25 (dd, J=4.0, 6.6 Hz, 1 H), 7.29 (d, A J=8.8 Hz, 1 H), 7.35 (dd, J=13.6, 8.4 Hz, 2 H).

EXAMPLE 20

5-Hydroxy-2-methyl-1-thiophen-2-ylmethyl-1H-indole-3-carboxylic Acid, 4-Methylbenzylamide (Compound 20)

$^1$H-NMR (METHANOL-$d_4$) δ 2.32 (s, 3 H), 2.64 (s, 3 H), 4.55 (s, 2 H), 5.52 (s, 2 H), 6.73 (dd, J=2.6, 8.8 Hz, 1 H), 6.91 (m, 2 H), 7.14 (d, J=2.2 Hz, 1 H), 7.15 (d, J=9 Hz, 2 H), 7.24-7.30 (m, 4 H).

EXAMPLE 21

5-Hydroxy-2-methyl-1-thiophen-2-ylmethyl-1H-indole-3-carboxylic Acid, 3-Chlorobenzylamide (Compound 21)

$^1$H-NMR (METHANOL-$d_4$) δ 2.65 (s, 3 H), 4.58 (s, 2 H), 5.53 (s, 2 H), 6.72 (dd, J=2.6, 8.8 Hz, 1 H), 6.91 (2 br d, 2 H), 7.16 (d, J=2.2 Hz, 1 H), 7.24-7.34 (m, 5 H), 7.42 (s, 1 H).

EXAMPLE 22

5-Hydroxy-2-methyl-1-thiophen-2-ylmethyl-1H-indole-3-carboxylic Acid, 4-Chlorobenzylamide (Compound 22)

$^1$H-NMR (METHANOL-$d_4$) δ 2.64 (s, 3 H), 4.57 (s, 2 H), 5.52 (s, 2 H), 6.72 (dd, J=2.6, 8.8 Hz, 1 H), 6.91 (2 br dd, 2 H), 7.15 (d, J=2.2 Hz, 1 H), 7.25 (dd, J=2.2, 4.0 Hz, 1 H), 7.29 (d, J=9 Hz, 1 H), 7.35 (d, J=8.4 Hz, 2 H), 7.40 (d, J=8.4 Hz, 2 H).

EXAMPLE 23

5-Hydroxy-2-methyl-1-thiophen-2-ylmethyl-1H-indole-3-carboxylic Acid, 2-methoxybenzylamide (Compound 23)

$^1$H-NMR (METHANOL-$d_4$) δ 2.64 (s, 3 H), 3.91 (s, 3 H), 4.60 (s, 2 H), 5.52 (s, 2 H), 6.72 (dd, J=2.6, 8.8 Hz, 1 H), 6.88-6.95 (m, 3 H), 7.00 (d, J=8.0 Hz, 1 H), 7.14 (d, J=2.2 Hz, 1 H), 7.24-7.35 (m, 4 H).

EXAMPLE 24

5-Hydroxy-2-methyl-1-thiophen-2-ylmethyl-1H-indole-3-carboxylic Acid, 3-Trifluoromethylbenzylamide (Compound 24)

$^1$H-NMR (METHANOL-$d_4$) δ 2.64 (s, 3 H), 4.67 (s, 2 H), 5.53 (s, 2 H), 6.73 (dd, J=2.6, 8.8 Hz, 1 H), 6.91 (m, 2 H), 7.17 (d, J=2.2 Hz, 1 H), 7.25 (dd, J=2.2, 4.0 Hz, 1 H), 7.30 (d, J=9.0 Hz, 1 H), 7.53 (m, 2 H), 7.70 (m, 2 H).

EXAMPLE 25

1-Benzyl-2-ethyl-5-hydroxy-1H-indole-3-carboxylic Acid, 3,4-Difluoro-benzylamide (Compound 25)

$^1$H-NMR (METHANOL-$d_4$) δ 1.13 (t, J=7.5 Hz, 3 H), 3.04 (q, J=7.5 Hz, 2 H), 4.58 (s, 2 H), 5.41 (s, 2 H), 6.64 (dd, J=2.6, 8.8 Hz, 1 H), 6.98 (2 br d, 2 H) 7.10 (d, J=8.8 Hz, 1 H), 7.17 (d, J=2.2 Hz, 1 H), 7.20-7.35 (m, 6 H).

EXAMPLE 26

1-Benzyl-2-ethyl-5-hydroxy-1H-indole-3-carboxylic Acid, 3-Methoxy-benzylamide (Compound 26)

$^1$H-NMR (METHANOL-$d_4$) δ 1.13 (t, J=7.5 Hz, 3 H), 3.04 (q, J=7.5 Hz, 2 H), 3.78 (s, 3 H), 4.60 (d, J=6.2 Hz, 2 H), 5.39 (s, 2 H), 6.64 (dd, J=2.6, 8.8 Hz, 1 H), 6.80 (br d, 1 H), 6.98 (2br d, 4 H), 7.08 (d, J=8.8 Hz, 1 H), 7.17 (d, J=2.2 Hz, 1 H), 7.22-7.25 (m, 4 H).

EXAMPLE 28

1-Benzyl-5-hydroxy-2-isopropyl-1H-indole-3-carboxylic Acid, 3,4-Difluorobenzamide (Compound 28)

$^1$H-NMR (CHLOROFORM-d) δ 1.34 (d, J=7.0 Hz, 6 H), 3.57-3.74 (m, 1 H), 4.51 (d, J=5.9 Hz, 2 H), 5.36 (s, 2 H), 6.38 (t, J=6.0 Hz, 1 H), 6.68 (dd, J=8.8, 2.3 Hz, 1 H), 6.87-6.95 (m, 3 H), 6.97-7.05 (m, 2 H), 7.05-7.16 (m, 2 H), 7.17-7.28 (m, 3 H).

EXAMPLE 32

1-Benzyl-2-ethyl-5-hydroxy-1H-indole-3-carboxylic Acid 3,5-Difluoro-benzylamide (Compound 32)

$^1$H-NMR (METHANOL-$d_4$) δ 1.13 (t, J=7.5 Hz, 3 H), 3.05 (q, J=7.5 Hz, 2 H), 4.61 (s, 2 H), 5.41 (s, 2 H), 6.68 (dd, J=2.2, 8.8 Hz, 1 H), 6.82 (m, 1 H), 7.00 (m, 4 H), 7.11 (d, J=8.8 Hz, 1 H), 7.18-7.30 (m, 4 H).

EXAMPLE 33

1-Benzyl-5-hydroxy-2-isopropyl-1H-indole-3-carboxylic Acid, 3,5-difluorobenzylamide (Compound 33)

$^1$H-NMR (CHLOROFORM-d) δ 1.39 (d, J=7.3 Hz, 6 H), 3.65-3.79 (m, 1 H), 4.68 (d, J=6.2 Hz, 2 H), 5.42 (s, 2 H), 6.32 (t, J=6.0 Hz, 1 H), 6.66-6.77 (m, 2 H), 6.89-6.98 (m, 4 H), 7.01 (d, J=8.8 Hz, 1 H), 7.13 (d, J=2.1 Hz, 1 H), 7.21-7.34 (m, 3 H).

EXAMPLE 34

1-Benzyl-5-hydroxy-2-isopropyl-1H-indole-3-carboxylic Acid, 3-methoxybenzylamide (Compound 34)

$^1$H-NMR (CHLOROFORM-d) δ 1.38 (d, J=7.0 Hz, 6 H), 3.80 (s, 3 H), 4.67 (d, J=5.9 Hz, 2 H), 5.39 (s, 2 H), 6.22 (t, J=5.6 Hz, 1 H), 6.67 (dd, J=8.6, 2.5 Hz, 1 H), 6.79-6.85 (m, 1 H), 6.89-7.02 (m, 5 H), 7.11 (d, J=2.3 Hz, 1 H), 7.20-7.32 (m, 4 H).

EXAMPLE 48

1-Benzyl-5-hydroxy-2-phenyl-1H-indole-3-carboxylic Acid, 3,5-Difluoro-benzylamide (Compound 48)

1H NMR (METHANOL-d) δ 4.39 (s, 2 H), 5.23 (s, 2 H), 6.67 (2d, J=8.4 Hz, 2 H), 6.79 (m, 2 H), 6.90 (2 d, 8.4 Hz, 2 H), 7.17 (d, J=8.4 Hz, 1 H), 7.22 (m, 3 H), 7.39-7.47 (m, 6 H).

The following compounds were prepared, by the General Procedures illustrated in Schemes 2 and 3, below, from ethyl 1-benzyl-2-methyl-1H-indole-3-carboxylate (Compound 57), which was synthesized as described in General Procedure 11:

EXAMPLE 36

1-Benzyl-2-methyl-1H-indole-3-carboxylic Acid, 3,5-Difluorobenzylamide (Compound 36)

$^1$H-NMR (CHLOROFORM-d) δ 2.72 (s, 3 H), 4.71 (d, J=3.9 Hz, 2 H), 5.37 (s, 2 H), 6.72 (dt, J=2.6, 8.8 Hz, 1 H), 6.97 (br dd, 3 H), 7.19-7.30 (m, 6 H), 7.72 (d, J=7.0 Hz, 1 H).

EXAMPLE 37

1-Benzyl-2-methyl-1H-indole-3-carboxylic Acid, 3,4-Difluorobenzylamide (Compound 37)

$^1$H-NMR (CHLOROFORM-d) δ 2.72 (s, 3 H), 4.68 (d, J=6.1 Hz, 2 H), 5.37 (s, 2 H), 6.33 (br s, 1 H), 6.99 (br d, 2 H), 7.14-7.30 (m, 9 H), 7.70 (d, J=6.6 Hz, 1 H).

EXAMPLE 38

1-Benzyl-2-methyl-1H-indole-3-carboxylic Acid, 3-Fluorobenzylamide (Compound 38)

$^1$H-NMR (CHLOROFORM-d) δ 2.73 (s, 3 H), 4.73 (d, J=5.7 Hz, 2 H), 5.37 (s, 2 H), 6.32 (br s, 1 H), 6.99 (br d, 3 H), 7.12-7.36 (m, 9 H), 7.72 (d, J=6.6 Hz, 1 H).

EXAMPLE 39

1-Benzyl-2-methyl-1H-indole-3-carboxylic Acid, 3-Methoxybenzylamide (Compound 39)

$^1$H-NMR (CHLOROFORM-d) δ 2.72 (s, 3 H), 3.82 (s, 3 H), 4.71 (d, J=5.8 Hz, 2 H), 5.36 (s, 2 H), 6.27 (br s, 1 H), 6.85

(dd, J=2.4. 8.8 Hz, 1 H), 7.00 (br d, 3 H), 7.17 (m, 2 H), 7.26-7.32 (m, 6 H), 7.72 (m, 1 H).

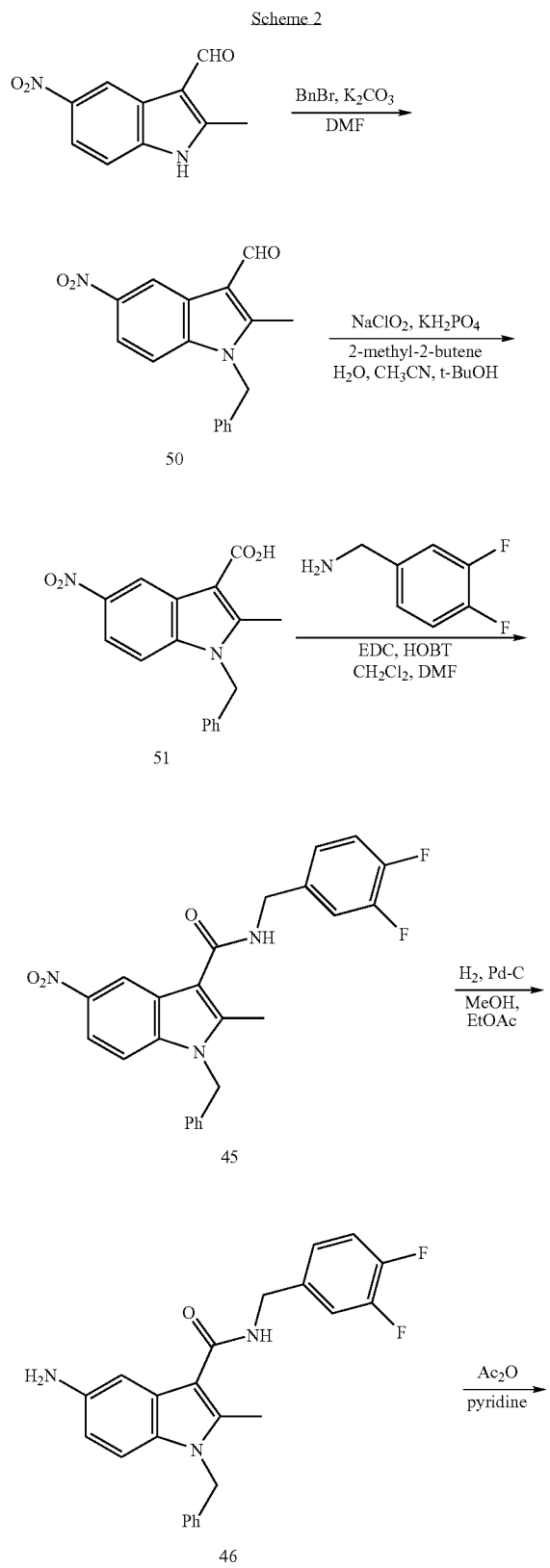

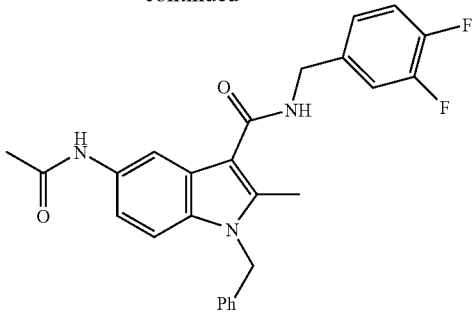

EXAMPLE 50

1-Benzyl-2-methyl-5-nitro-1H-indole-3-carboxalde-hyde (Compound 50)

General Procedure 4. To a solution of 2-methyl-5-nitro-1H-indole-3-carboxaldehyde (500 mg, 2.45 mmol) in DMF (5 ml) was added potassium carbonate (1.0 g, 7.35 mmol) and benzyl bromide (0.44 ml, 3.68 mmol). The mixture was stirred at room temperature for 4 h, diluted with EtOAc, washed with $H_2O$, brine, dried over $Na_2SO_4$, and concentrated under reduced pressure. The residue was triturated with $Et_2O$-hexane to yield 1-benzyl-2-methyl-5-nitro-1H-indole-3-carboxaldehyde (Compound 50) as a yellow solid (600 mg, 83%).

$^1$H-NMR (METHANOL-$d_4$) δ 2.76 (s, 3 H), 5.60 (s, 2 H), 7.04-7.11 (m, 2 H), 7.26-7.37 (m, 3 H), 7.60 (d, J=9.1 Hz, 1 H), 8.15 (dd, J=8.9, 2.2 Hz, 1 H), 9.11 (d, J=2.3 Hz, 1 H), 10.20 (s, 1 H).

EXAMPLE 51

1-Benzyl-2-methyl-5-nitro-1H-indole-3-carboxylic Acid (Compound 51)

General Procedure 5. To a suspension of 1-benzyl-2-methyl-5-nitro-1H-indole-3-carboxaldehyde (Compound 50, 150 mg, 0.51 mmol) in acetonitrile (6 ml), tert-butanol (6 ml) and $H_2O$ (6 ml) was added 2-methyl-2-butene (4 ml), potassium phosphate monobasic (1.4 g, 10.2 mmol), sodium chlorite (80%, 1.15 g, 10.2 mmol). The mixture was stirred at room temperature for 20 h, more potassium phosphate monobasic (0.35 g, 2.6 mmol) and sodium chlorite (80%, 0.29 g, 2.6 mmol) were added and stirred at room temperature for 24 h. The solvent was removed under reduced pressure. The residue solid was washed with $H_2O$ (×3) and filtered, dissolved in acetone and filtered to yield 1-benzyl-2-methyl-5-nitro-1H-indole-3-carboxylic acid (Compound 51) as a yellow powder (160 mg, 100%). $^1$H-NMR (ACETONE-$d_6$) δ 2.83 (s, 3 H), 5.68 (s, 2 H), 7.06-7.15 (m, 2 H), 7.25-7.41 (m, 3 H), 7.68 (d, J=9.1 Hz, 1 H), 8.10 (dd, J =9.1, 2.3 Hz, 1 H), 9.11 (d, J=2.3 Hz, 1 H).

EXAMPLE 45

1-Benzyl-2-methyl-5-nitro-1H-indole-3-carboxylic Acid, 3,4-Difluorobenzylamide (Compound 45)

The title compound was prepared from 1-benzyl-2-methyl-5-nitro-1H-indole-3-carboxylic acid (Compound 51) by General Procedure 3.

$^1$H-NMR (DMSO-d$_6$) δ 2.60 (s, 3 H), 4.51 (d, J=6.2 Hz, 2 H), 5.60 (s, 2 H), 7.01-7.08 (m, 2 H), 7.20-7.49 (m, 6 H), 7.74 (d, J=8.8 Hz, 1 H), 8.05 (dd, J=9.1, 2.3 Hz, 1 H), 8.57 (t, J=5.7 Hz, 1 H), 8.71 (d, J=2.1 Hz, 1 H).

EXAMPLE 52

1-Benzyl-5-(benzyloxy)-1H-indole-3-carboxylic Acid, N-(3,4-difluorobenzyl)-(Compound 52)

The title compound was prepared from 5-(benzyloxy)-1H-indole-3-carboxaldehyde by, in order, General Procedures 4, 5, and 3.

$^1$H-NMR (METHANOL-d$_4$) δ 4.53 (s, 2 H), 5.11 (s, 2 H), 5.39 (s, 2 H), 6.92 (dd, J=9.1, 2.3 Hz, 1 H), 7.14-7.39 (m, 12 H), 7.43-7.49 (m, 2 H), 7.79 (d, J=2.3 Hz, 1 H), 7.91 (s, 1 H).

EXAMPLE 46

5-Amino-1-benzyl-2-methyl-1H-indole-3-carboxylic Acid, 3,4-Difluorobenzylamide (Compound 46)

General Procedure 6. To a solution of 1-benzyl-2-methyl-5-nitro-1H-indole-3-carboxylic acid, 3,4-difluorobenzylamide (Compound 45, 97 mg, 0.22 mmol) in MeOH (20 ml) and EtOAc (20 ml) was added Pd—C (10%, 47 mg, 0.045 mmol). The reaction was stirred under hydrogen for 24 h, filtered through Celite, washed with MeOH-EtOAc (1:1) to yield 5-amino-1-benzyl-2-methyl-1H-indole-3-carboxylic acid, 3,4-difluorobenzylamide (Compound 46) as a white solid (93 mg, 100%).

$^1$H-NMR (METHANOL-d$_4$) δ 2.54 (s, 3 H), 4.58 (s, 2 H), 5.35 (s, 2 H), 6.69 (dd, J=8.5, 2.1 Hz, 1 H), 6.95-7.01 (m, 2 H), 7.12 (d, J=8.5 Hz, 1 H), 7.16-7.36 (m, 6 H).

EXAMPLE 27

1-Benzyl-5-hydroxy-1H-indole-3-carboxylic Acid, 3,4-Difluorobenzylamide (Compound 27)

The title compound was prepared from 1-benzyl-5-(benzyloxy)-1H-indole-3-carboxylic acid, 3,4-difluorobenzylamide (Compound 52) by General Procedure 6.

$^1$H-NMR (METHANOL-d$_4$) δ 4.52 (s, 2 H), 5.36 (s, 2 H), 6.74 (dd, J=8.8, 2.6 Hz, 1 H), 7.12-7.36 (m, 9 H), 7.54 (d, J=2.1 Hz, 1 H), 7.86 (s, 1 H).

EXAMPLE 47

5-Acetamido-1-benzyl-2-methyl-1H-indole-3-carboxylic Acid, 3,4-Difluorobenzylamide (Compound 47)

General Procedure 7. To a solution of 5-amino-1-benzyl-2-methyl-1H-indole-3-carboxylic acid, 3,4-difluorobenzylamide (Compound 46, 50 mg, 0.12 mmol) in pyridine (3 ml) was added acetic anhydride (120 μl, 1.23 mmol). The reaction was stirred at room temperature for 72 h, diluted with EtOAc, washed successively with 1M HCl, H$_2$O, brine, dried over Na$_2$SO$_4$, and concentrated under reduced pressure. The residue was crystallized from CH$_2$Cl$_2$-Et$_2$O to yield 5-acetamido-1-benzyl-2-methyl-1H-indole-3-carboxylic acid, 3,4-difluorobenzylamide (Compound 47) as a white solid (37 mg, 68%).

$^1$H-NMR (METHANOL-d$_4$) δ 2.13 (s, 3 H), 2.58 (s, 3 H), 4.59 (s, 2 H), 5.44 (s, 2 H), 6.96-7.04 (m, 2 H), 7.14-7.37 (m, 9 H), 7.99 (d, J=2.1 Hz, 1 H).

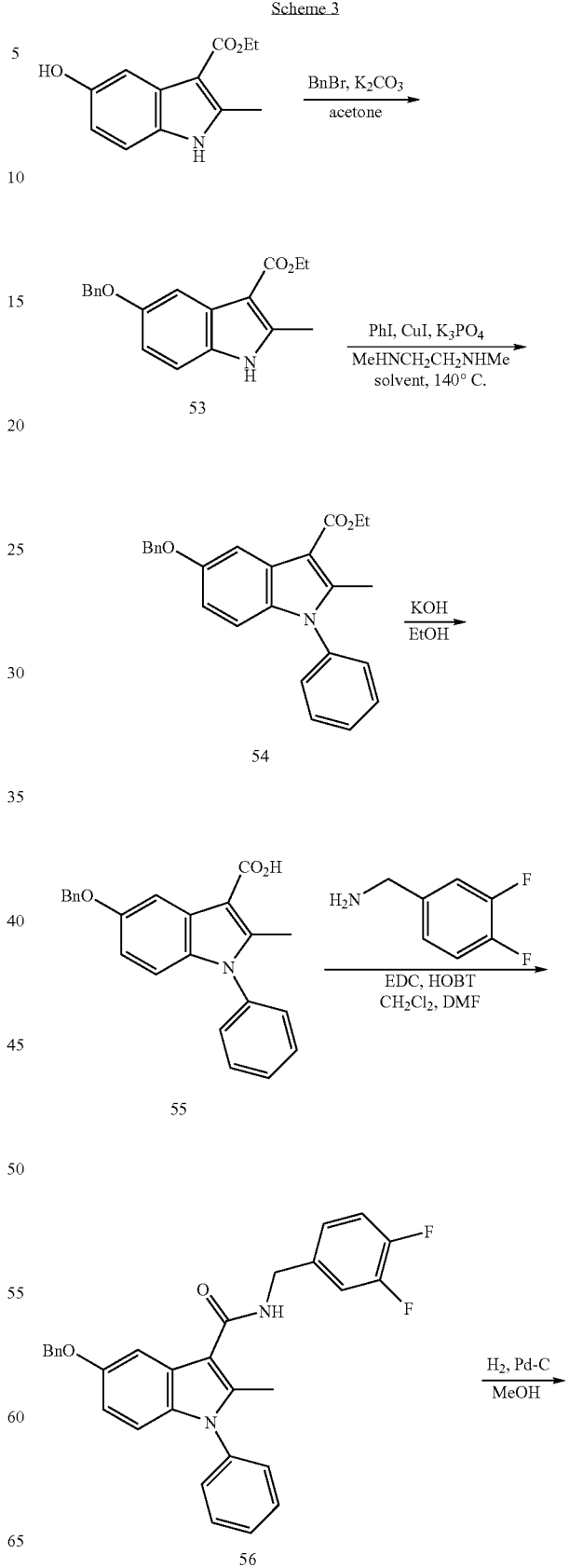

Scheme 3

-continued

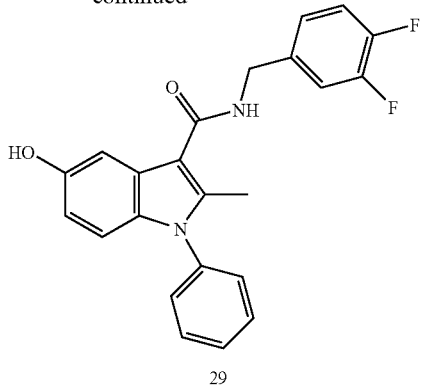

29

EXAMPLE 53

5-Benzyloxy-2-methyl-1H-indole-3-carboxylic Acid, Ethyl Ester (Compound 53)

General Procedure 8. To a mixture of 5-hydroxy-2-methyl-1H-indole-3-carboxylic acid, ethyl ester (0.76 g, 3.47 mmol) and potassium carbonate (0.92 g, 6.67 mmol) in acetonitrile (10 ml) was added benzyl bromide (1.0 ml, 1.4 g, 8.4 mmol). The mixture was heated at 75-80° C. for 18 h. The reaction was cooled to room temperature, quenched with water, extracted with EtOAc, washed with brine, dried over $Na_2SO_4$, and concentrated under reduced pressure. The residue was purified by flash column chromatography on silica gel (30% EtOAc-hexanes) to yield 5-benzyloxy-2-methyl-1H-indole-3-carboxylic acid, ethyl ester (Compound 53) as a yellow solid (0.56 g, 52%).

$^1$H-NMR (METHANOL-$d_4$) δ 1.39 (t, J=7.0 Hz, 3 H), 2.64 (s, 3 H), 4.32 (q, J=7.0 Hz, 2 H), 5.10 (s, 2 H), 6.84 (dd, J=2.2, 8.8 Hz, 1 H), 7.20 (d, J=8.8 Hz, 1 H), 7.23-7.40 (m, 5 H), 7.45 (2 br d, 2 H), 7.58 (d, 2.2 Hz, 1 H).

EXAMPLE 54

5-Benzyloxy-2-methyl-1-phenyl-1H-indole-3-carboxylic Acid, Ethyl Ester (Compound 54)

General Procedure 9. To a mixture of 5-benzyloxy-2-methyl-1H-indole-3-carboxylic acid, ethyl ester (Compound 53, 0.14 g, 0.45 mmol) in toluene (6 ml) having been degassed under argon for 15 min. was added 2-iodo-benzene (0.10 ml, 0.48 g, 0.88 mmol), potassium phosphate (0.20 g, 0.94 mmol), copper (I) iodide (24 mg, 0.13 mmol), and then N,N'-dimethylethylenediamine (12 mg, 0.14 mmol) with continued degassing. The tube was then sealed and mixture was heated at 140° C. for 24 h. The reaction was then cooled and filtered. The filtrate was concentrated under reduced pressure and the crude product residue was purified by flash column chromatography on silica gel (30% EtOAc-hexanes) to yield 5-benzyloxy-2-methyl-1-phenyl-1H-indole-3-carboxylic acid, ethyl ester (Compound 54) as an orange oil (0.13 g, 76%).

$^1$H-NMR (CHLOROFORM-d) δ 1.44 (t, J=7.0 Hz, 3 H), 2.57 (s, 3 H), 4.42 (q, J=7.0 Hz, 2 H), 5.16 (s, 2 H), 6.86 (dd, J=2.7, 8.8 Hz, 1 H), 6.92 (d, J=8.8 Hz, 1 H), 7.25-7.41 (m, 5 H), 7.48-7.60 (m, 5 H), 7.78 (d, J=2.7 Hz, 1 H).

EXAMPLE 55

5-Benzyloxy-2-methyl-1-phenyl-1H-indole-3-carboxylic Acid (Compound 55)

The title compound was prepared from 5-benzyloxy-2-methyl-1-phenyl-1H-indole-3-carboxylic acid, ethyl ester (Compound 54) by General Procedure 2.

$^1$H-NMR (METHANOL-$d_4$) δ 2.60 (s, 3 H), 5.12 (s, 2 H), 6.84 (dd, J=2.6, 8.8 Hz, 1 H), 6.90 (d, J=8.8 Hz, 1 H), 7.26-7.63 (m, 10 H), 7.77 (d, J=2.6 Hz, 1 H).

EXAMPLE 56

5-Benzyloxy-2-methyl-1-phenyl-1H-indole-3-carboxylic Acid, 3,4-difluorobenzylamide (Compound 56)

The title compound was prepared from 5-benzyloxy-2-methyl-1-phenyl-1H-indole-3-carboxylic acid (Compound 55) by General Procedure 3.

$^1$H-NMR (METHANOL-$d_4$) δ 2.44 (s, 3 H), 4.60 (s, 2 H), 5.10 (s, 2 H), 6.85 (dd, J=2.2, 8.8 Hz, 1 H), 6.90 (d, J=8.8 Hz, 1 H), 7.21-7.45 (m, 8 H), 7.54-7.66 (m, 3 H).

EXAMPLE 29

5-Hydroxy-2-methyl-1-phenyl-1H-indole-3-carboxylic Acid 3,4-Difluoro-benzylamide (Compound 29)

General Procedure 10. To a mixture of 5-benzyloxy-2-methyl-1-phenyl-1H-indole-3-carboxylic acid, 3,4-difluorobenzylamide (Compound 56, 0.15 g, 0.31 mmol) in methanol (15 ml), which was degassed with argon for 10 min, was added 10% palladium on carbon (0.17 g), with continued degassing. The reaction was placed in par tube on hydrogenator and hydrogenated at 45 psi for 18 h. The reaction was then filtered, concentrated under reduced pressure and the crude product residue was purified by flash column chromatography on silica gel (30% EtOAc-hexanes) to yield 5-hydroxy-2-methyl-1-phenyl-1H-indole-3-carboxylic acid, 3,4-difluorobenzylamide (Compound 29) as a solid (0.11 g, 92%).

$^1$H-NMR (METHANOL-$d_4$) δ 2.42 (s, 3 H), 4.59 (s, 2 H), 6.66 (dd, J=2.2, 8.8 Hz, 1 H), 6.82 (d, J=8.8 Hz, 1 H), 7.21-7.26 (m, 3 H), 7.30-7.40 (m, 3 H), 7.53-7.65 (m, 3 H).

EXAMPLE 30

5-Hydroxy-2-methyl-1-pyridin-2-yl-1H-indole-3-carboxylic Acid 3,4-Difluoro-benzylamide (Compound 30)

The title compound was prepared from 2-iodo-pyridine by following, in order, General procedures 8, 9, 2, 3 and 10.

$^1$H-NMR (METHANOL-$d_4$) δ 2.51 (s, 3 H), 4.59 (s, 2 H), 6.70 (dd, J=2.6, 8.8 Hz, 1 H), 7.03 (d, J=8.8 Hz, 1 H), 7.20-7.26 (m, 3 H), 7.33 (m, 1 H), 7.55 (m, 2 H), 8.10 (dt, J=2.2, 8.8 Hz, 1 H), 8.65 (dd, J=2.2, 5.7 Hz, 1 H).

EXAMPLE 31

5-Hydroxy-2-methyl-1-thiophen-2-yl-1H-indole-3-carboxylic Acid 3,4-Difluorobenzylamide (Compound 31)

The title compound was prepared from 2-iodothiophene by following, in order, General Procedures 8, 9, 2, 3 and 10.

$^1$H-NMR (METHANOL-$d_4$) δ 2.45 (s, 3 H), 4.58 (s, 2 H), 6.70 (dd, J=2.6, 8.8 Hz, 1 H), 6.94 (d, J=8.8 Hz, 1 H), 7.12 (dd, J=1.3, 3.5 Hz, 1 H), 7.16-7.46 (m, 5 H), 7.55 (dd, J=1.4, 5.7 Hz, 1 H).

EXAMPLE 35

5-Methoxy-2-methyl-1-phenyl-1H-indole-3-carboxylic Acid, 3,5-Difluorobenzylamide (Compound 35)

The title compound was prepared from methyl iodide by following, in order, General Procedures 8, 9, 2 and 3.

$^1$H-NMR (CHLOROFORM-d) δ 2.55 (s, 3 H), 3.85 (s, 3 H), 4.72 (d, J=6.1 Hz, 2 H), 6.25 (br s, 1 H), 6.73 (m, 1 H), 6.80 (dd, J=2.2, 8.8 Hz, 1 H), 6.97 (2d, J=8.8 Hz, 3 H), 7.26-7.33 (m, 3 H), 7.51-7.60 (m, 3 H).

EXAMPLE 40

5-Methoxy-1,2-dimethyl-1H-indole-3-carboxylic Acid, 3,5-difluoro-benzylamide (Compound 40)

The title compound was prepared from methyl iodide by following, in order, General procedures 8, 9, 2 and 3.

$^1$H-NMR (CHLOROFORM-d) δ 2.73 (s, 3 H), 3.69 (s, 3 H), 3.84 (s, 3 H), 4.69 (d, J=6.1 Hz, 2 H), 6.19 (br s, 1 H), 6.71 (dt, J=2.2, 8.8 Hz, 1 H), 6.91 (dd, J=2.2 8.8 Hz, 1 H), 6.95 (br d, 2 H), 7.19 (d, J=2.2 Hz, 1 H), 7.21-7.26 (m, 1 H).

EXAMPLE 41

5-Methoxy-1,2-dimethyl-1H-indole-3-carboxylic Acid 3-Fluorobenzylamide (Compound 41)

The title compound was prepared from methyl iodide by following, in order, General Procedures 8, 9, 2 and 3.

$^1$H-NMR (CHLOROFORM-d) δ 2.73 (s, 3 H), 3.68 (s, 3 H), 3.81 (s, 3 H), 4.71 (d, J=6.1 Hz, 2 H), 6.15 (br s, 1 H), 6.87 (dd, J=2.2, 8.8 Hz, 1 H), 6.97 (m, 2 H), 7.13 (2 br d, 1 H), 7.18 (d, J=2.6 Hz, 1 H), 7.22 (d, J=8.4 Hz, 2 H).

EXAMPLE 49

5-Benzyloxy-2-methyl-1-pyridin-2-yl-1H-indole-3-Carboxylic Acid, 3,4-Difluorobenzylamide (Compound 49)

The title compound was prepared from 2-iodopyridine by following, in order, General Procedures 8, 9, 2 and 3.

$^1$H-NMR (CHLOROFORM-d) δ 2.52 (s, 3 H), 4.60 (s, 2 H), 5.10 (s, 2 H), 6.89 (dd, J=2.6, 8.8 Hz, 1 H), 7.10 (d, J=8.8 Hz, 1 H), 7.21-7.45 (m, 6 H), 7.55 (2 br, d, 2 H), 8.10 (dt, J=2.2, 7.9 Hz, 1 H), 8.65 (m, 1 H).

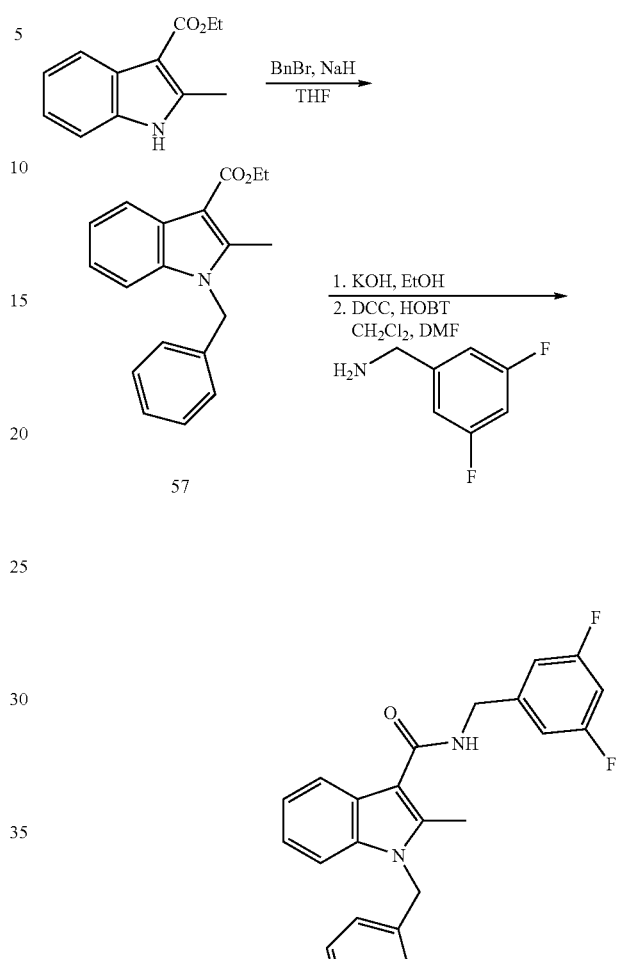

EXAMPLE 57

1-Benzyl-2-methyl-1H-indole-3-carboxylic Acid, Ethyl Ester (Compound 57)

General Procedure 11.-To a mixture of sodium hydride (0.28 g, 60% in mineral oil, 0.17g, 7.0 mmol) in 10 ml of tetrahydrofuran stirring at 0° C. under argon, was added 2-methyl-1H-indole-3-carboxylic acid ethyl ester (1.17 g, 5.8 mmol) and the solution was stirred at 0° C. for 15 min. Benzyl bromide (0.80 ml, 1.15 g, 6.7 mmol) was then added and the reaction allowed to warm to room temperature and stirred for 24 h. The reaction was cooled to 0° C., quenched with water, extracted with EtOAc, washed with brine, dried over $Na_2SO_4$, and concentrated under reduced pressure. The residue was purified by flash column chromatography on silica gel (40% EtOAc-hexanes) to yield 1-benzyl-2-methyl-1H-indole-3-carboxylic acid, ethyl ester (Compound 57) as a tan solid (1.13 g, 67%).

¹H-NMR (CHLOROFORM-d) δ 1.46 (t, J=7.0 Hz, 3 H), 2.73 (s, 3 H), 4.42 (q, J=7.0 Hz, 2 H), 5.36 (s, 2 H), 6.97 (dd, J=2.1, 8.8 Hz, 2 H), 7.15-7.30 (m, 6 H), 8.17 (d, J=8.5 Hz, 1 H).

EXAMPLE 42

2-Methyl-1-thiophen-2-ylmethyl-1H-indole-3-carboxylic Acid, 3,4-difluorobenzylamide (Compound 42)

The title compound was prepared from 2-bromomethylthiophene by following, in order, General Procedures 11, 2 and 3.

¹H-NMR (CHLOROFORM-d) δ 2.81 (s, 3 H), 4.66 (s, 2 H), 5.49 (s, 2 H), 6.29 (br s, 1 H), 6.83 (br d, 1 H), 6.91 (m, 1 H), 7.12-7.26 (m, 4 H), 7.42 (m, 2 H), 7.68 (m, 2 H).

EXAMPLE 43

2-Methyl-1-thiophen-2-ylmethyl-2H-indole-3-carboxylic Acid, 3-Methoxybenzylamide (Compound 43)

The title compound was prepared from 2-bromomethylthiophene by following, in order, General Procedures 11, 2 and 3.

¹H-NMR (CHLOROFORM-d) δ 1.56 (s, 3 H), 2.81 (s, 2 H), 3.81 (s, 3 H), 4.69 (d, J=5.7 Hz, 1 H), 5.48 (s, 2 H), 6.25 (br t, 1H), 6.72 (dd, J=2.6, 8.8 Hz, 1 H), 6.88-6.95 (m, 3 H), 7.00 (d, J=8.0 Hz, 1 H), 7.14 (d, J=2.2 Hz, 1 H), 6.84 (br d, 2 H), 6.91 (m, 1 H), 6.99 (m, 2 H), 7.17-7.22 (m, 3 H), 7.30 (d, J=8.0 Hz, 1 H), 7.39 (d, J=7.0 Hz, 1 H), 7.68 (d, J=2.2 Hz, 1 H).

EXAMPLE 44

2-Methyl-1-thiophen-2-ylmethyl-1H-indole-3-carboxylic Acid 3,5-Difluorobenzylamide (Compound 44)

The title compound was prepared from 2-bromomethylthiophene by following, in order, General Procedures 11, 2 and 3.

¹H-NMR (METHANOL-d₄) δ 2.63 (s, 3 H), 4.58 (s, 2 H), 5.53 (s, 2 H), 6.72 (dd, J=2.6, 8.8 Hz, 1 H), 6.91 (2 br d, 2 H), 7.06 (t, J=8.8 Hz, 2 H), 7.15 (d, J=2.2 Hz, 1 H), 7.25 (dd, J=4.0, 6.6 Hz, 1 H), 7.29 (d, J=8.8 Hz, 1 H), 7.35 (dd, J=13.6, 8.4 Hz, 2 H).

The foregoing description details specific methods and compositions that can be employed to practice the present invention, and represents the best mode contemplated. Thus, however detailed the foregoing may appear in text, it should not be construed as limiting the overall scope hereof, rather, the ambit of the present invention was to be governed only by the lawful construction of the appended claims.

What is claimed is:
1. A compound having the structure:

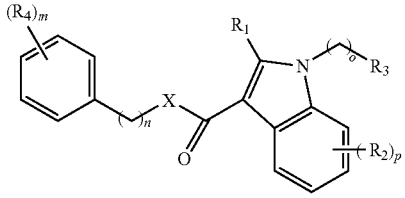

wherein:
$R_1$ is selected from the group consisting of methyl, ethyl, i-propyl and phenyl;
$R_2$ is selected from the group consisting of hydroxyl, C1-C12 alkoxy, amino, or nitro;
$R_3$ is selected from the group consisting of $C_1$ to $C_6$ alkyl, phenyl, thiophenol, pyridinyl, and furanyl;
$R_4$ is selected from the group consisting of alkyl, chloro, trifluoromethyl, methoxy and fluoro;
X is O or $NR_5$ wherein $R_5$ is H or alkyl;
n, o, and p are 0 to 4; and
m is 0 to 5.

2. The compound of claim 1 selected from the group consisting of
1-Benzyl-5-hydroxy-2-methyl-1H-indole-3-carboxylic Acid, 3,5-Difluorobenzylamide;
5-Hydroxy-2-methyl-1-thiophen-2-ylmethyl-1H-indole-3-carboxylic Acid, 3,4-Difluorobenzylamide;
1-Butyl-5-hydroxy-2-methyl-1H-indole-3-carboxylic Acid, 3,5-Difluoro-benzylamide;
1-Furan-2-ylmethyl-5-hydroxy-2-methyl-1H-indole-3-carboxylic Acid, 3,4-Difluorobenzylamide;
5-Hydroxy-2-methyl-1-thiophen-2-ylmethyl-1H-indole-3-carboxylic Acid, 3,5-Difluorobenzylamide;
1-Furan-2-ylmethyl-5-hydroxy-2-methyl-1H-indole-3-carboxylic Acid 3,5-Difluorobenzylamide;
1-Benzyl-5-hydroxy-2-methyl-1H-indole-3-carboxylic Acid 3, 4-Difluoro-benzylamide;
5-Hydroxy-2-methyl-1-thiophen-2-ylmethyl-1H-indole-3-carboxylic Acid, 3-Fluorobenzylamide;
5-Hydroxy-2-methyl-1-thiophen-2-ylmethyl-1H-indole-3-carboxylic Acid, Benzylamide;
5-Hydroxy-2-methyl-1-thiophen-2-ylmethyl-1H-indole-3-carboxylic Acid, 3-Methoxybenzylamide;
1-Butyl-5-hydroxy-2-methyl-1H-indole-3-carboxylic Acid, 3-Methoxy-benzylamide;
5-Hydroxy-2-methyl-1-thiophen-2-ylmethyl-1H-indole-3-carboxylic Acid, 4-Fluorobenzylamide;
5-Hydroxy-2-methyl-1-thiophen-2-ylmethyl-1H-indole-3-carboxylic Acid, 4-Methylbenzylamide;
5-Hydroxy-2-methyl-1-thiophen-2-ylmethyl-1H-indole-3-carboxylic Acid, 3-Chlorobenzylamide;
5-Hydroxy-2-methyl-1-thiophen-2-ylmethyl-1H-indole-3-carboxylic Acid, 4-Chlorobenzylamide;
5-Hydroxy-2-methyl-1-thiophen-2-ylmethyl-1H-indole-3-carboxylic Acid, 2-methoxybenzylamide;
1-Benzyl-2-ethyl-5-hydroxy-1H-indole-3-carboxylic Acid, 3,4-Difluoro-benzylamide;
1-Benzyl-2-ethyl-5-hydroxy-1H-indole-3-carboxylic Acid, 3-Methoxy-benzylamide;
1-Benzyl-5-hydroxy-2-isopropyl-1H-indole-3-carboxylic Acid, 3,4-Difluorobenzamide;
5-Hydroxy-2-methyl-1-phenyl-1H-indole-3-carboxylic Acid 3,4-Difluoro-benzylamide;

5-Hydroxy-2-methyl-1-pyridin-2-yl-1H-indole-3-carboxylic Acid 3,4-Difluoro-benzylamide;
5-Hydroxy-2-methyl-1-thiophen-2-yl-1H-indole-3-carboxylic Acid 3,4-Difluorobenzylamide;
1-Benzyl-2-ethyl-5-hydroxy-1H-indole-3-carboxylic Acid 3,5-Difluoro-benzylamide;
1-Benzyl-5-hydroxy-2-isopropyl-1H-indole-3-carboxylic Acid, 3,5-difluorobenzylamide;
1-Benzyl-5-hydroxy-2-isopropyl-1H-indole-3-carboxylic Acid, 3-methoxybenzylamide; and
1-Benzyl-5-hydroxy-2-phenyl-1H-indole-3-carboxylic Acid, 3,5-Difluoro-benzylamide.

3. The compound of claim 2 selected from the group consisting of 1-Benzyl-5-hydroxy-2-methyl-1H-indole-3-carboxylic Acid, 3,5-Difluorobenzylamide;
1-Furan-2-ylmethyl-5-hydroxy-2-methyl-1H-indole-3-carboxylic Acid 3,5-Difluorobenzylamide;
5-Hydroxy-2-methyl-1-thiophen-2-ylmethyl-1H-indole-3-carboxylic Acid, 3-Methoxybenzylamide;
1-Benzyl-2-ethyl-5-hydroxy-1H-indole-3-carboxylic Acid, 3,4-Difluoro-benzylamide;
1-Benzyl-2-ethyl-5-hydroxy-1H-indole-3-carboxylic Acid 3,5-Difluoro-benzylamide;
1-Benzyl-5-hydroxy-2-isopropyl-1H-indole-3-carboxylic Acid, 3,5-difluorobenzylamide;
1-Benzyl-5-hydroxy-2-isopropyl-1H-indole-3-carboxylic Acid, 3-methoxybenzylamide; and
1-Benzyl-5-hydroxy-2-phenyl-1H-indole-3-carboxylic Acid, 3,5-Difluoro-benzylamide.

\* \* \* \* \*